US00PP22171P3

(12) United States Plant Patent
Austin

(10) Patent No.: US PP22,171 P3
(45) Date of Patent: Oct. 4, 2011

(54) ***ROSA HYBRIDA* SHRUB NAMED 'AUSNYSON'**

(50) Latin Name: *Rosa hybrida shrub.*
Varietal Denomination: AUSnyson

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 0 days.

(21) Appl. No.: 12/800,498

(22) Filed: May 17, 2010

(65) Prior Publication Data

US 2011/0197321 P1 Aug. 11, 2011

(30) Foreign Application Priority Data

Feb. 11, 2010 (GB) ..... AFP 5/2117

(51) Int. Cl.
*A01H 5/00* (2006.01)

(52) U.S. Cl. ..... Plt./102

(58) Field of Classification Search ..... Plt./102
See application file for complete search history.

*Primary Examiner* — Annette Para
(74) *Attorney, Agent, or Firm* — Kauth, Pomeroy, Peck & Bailey LLP

(57) ABSTRACT

A variety of rose plant of the shrub class, named 'AUSnyson'. The 'AUSnyson' rose is a plant suitable for repeat flowering production having rich orange-red buds that open to form blooms with loosely-arranged petals having a salmon-pink upper side coloring and golden-yellow reverse side coloring with a strong tea fragrance and slightly arching growth.

1 Drawing Sheet

Classification: The present invention relates to a new *Rosa hybrida* shrub.

Variety denomination: The new plant has the varietal denomination 'AUSnyson'.

CROSS-REFERENCE TO RELATED APPLICATIONS

The current application claims priority to a United Kingdom Breeder's Right Certificate Application No. AFP 5/2117, filed Feb. 11, 2010, the disclosure of which is incorporated herein by reference.

ORIGIN OF INVENTION

This invention relates to a new and distinct variety of shrub rose plant named 'AUSnyson', which was originated by crossing two unnamed, unpatented varieties of *Rosa hybrida.*

BACKGROUND OF THE INVENTION

The primary objective of this breeding was to produce a robust disease-resistant flowering variety having rich orange-red buds that open to form blooms with loosely-arranged petals having a salmon-pink upper side coloring and golden-yellow reverse side coloring with a strong tea fragrance and slightly arching growth.

SUMMARY OF THE INVENTION

Among the features which distinguish the new variety from other presently available and commercial rose cultivars known to the inventor is the following combination of characteristics: superb disease resistance, orange-red buds that open to form blooms with loosely-arranged petals having a salmon-pink upper side coloring and golden-yellow reverse side coloring, a large bushy shrub with slightly arching stems, and mid-green leaves with slightly bronze tones when young.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSnyson' may be asexually propagated by budding and grafting. The budding and grafting successfully occurred on the plant/rootstock *Rosa* cv. 'Dr. Huey' in the United States and on the plant/rootstock *Rosa dumetorum* cv. 'Laxa' in the United Kingdom.

COMPARISON WITH PARENTS

The new rose may be distinguished from its seed parent, by the following combination of characteristics: whereas the seed parent is not as disease resistant and has fuller yellow blooms, 'AUSnyson' is vigorously disease resistant and bears flowers of orange-red buds that open to form blooms with loosely-arranged petals having a salmon-pink upper side coloring and golden-yellow reverse side coloring and a strong tea fragrance. The new variety is classified as a *hybrida* rose with a slightly arched growing habit.

The new variety may be distinguished from its pollen parent, by the following combination of characteristics: whereas the pollen parent is of an overall poorer quality, 'AUSnyson' is vigorous and has superb disease resistance.

COMPARISON WITH THE CLOSEST COMMERCIALLY AVAILABLE CULTIVAR

The closest commercially available cultivar to the new variety is the 'AUSmum' (U.S. Plant Pat. No. 9,527). The new rose may be distinguished from the 'AUSmum' variety by the following combination of characteristics: the 'AUSmum' produces blooms having a deep cup with a greater number of petals that have a bright copper upper side and a pale copper yellow underside, compared to 'AUSnyson', which produces open-cup blooms having a salmon-pink upper side and a golden-yellow reverse side. In addition, the foliage of the 'AUSmum' is darker green compared to that of 'AUSnyson'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society [2001] except where common terms of color definition are employed.

DESCRIPTION OF THE NEW VARIETY

The following description is of 2 year-old rose plants of the new variety grown outdoors in Albrighton, Britain in the month of July. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:
- *Size.*—About 2 cm long and 3 cm in diameter when the petals start to unfurl.
- *Form.*—The bud form is short.
- *Color.*—When sepals first divide, the bud color is red RHS 53A, with red flecks. When half blown, the upper sides of the petals are red RHS 53A, and the lower sides of the petals are red RHS 42A.
- *Calyx.*—Shape: (from above) pitcher-shaped. Length: 5 cm. Diameter: 5 cm.
- *Sepals.*—Arrangement: Regular. Color: Upper Surface: yellow-green RHS N144. Lower Surface: yellow-green RHS N144. Length: 2 cm. Width: 1 cm. Shape: Pointed. Margin: N/A. Surface texture: Upper Surface: Mossy. Lower Surface: Smooth. Number: There are three lightly appendaged sepals. There are 2 unappendaged sepals with smooth edges.
- *Receptacles.*—Color: yellow-green RHS N144B. Shape: pitcher. Size: small, about 1 cm×1 cm. Surface: Smooth.
- *Peduncle.*—Length: medium, averaging about 5 cm. Surface: smooth. Color: bronzy RHS 183C. Strength: Normal.

Blooms:
- *Size.*—Medium, average open diameter is about 7.5 cm.
- *Borne.*—Several together (4-14) blooms having irregular shape.
- *Stems.*—Strength: Normal, average length is about 5 cm. Diameter: 5 mm.
- *Form.*—When first open, bloom is cupped. Permanence of bloom: outer petals curl back.

Petalage: Number of petals under normal conditions: 57.
- *Color.*—The upper sides of the petals are salmon pink RHS Group 34C. The reverse sides of the petals are yellow RHS 18A. The base of the petals has a spot of yellow RHS 9A on both sides.
- *Discoloration.*—General tonality at end of first day is salmon pink RHS 34C.
- *Fragrance.*—Strong. Character of fragrance: Myrrh.

Petals:
- *Texture.*—Smooth.
- *Size.*—Width: 40 mm. Length: 35 mm.
- *Surface.*—Smooth.
- *Shape.*—Round.
- *Margin.*—Medium reflexing with medium undulation.
- *Apex shape.*—Round.
- *Base shape.*—Rounded outer petals, inner petal more pointed.
- *Form.*—Incurved.
- *Arrangement.*—Irregular.
- *Petaloids.*—Number: None.
- *Persistence.*—Petals hang on and dry.
- *Lastingness.*—On the plant: long, about 5 days. As a cut flower: not tested.

Reproductive parts:
- *Stamens.*—Number: ~95. Length: 1 cm.
- *Anthers.*—Length: 2 mm. Color: yellow-orange RHS 22A. Arrangement: Regular around styles.
- *Filaments.*—Color: yellow-orange RHS 21A. Length: 10 mm.
- *Pollen.*—Color: yellow-orange RHS 21A.
- *Pistils.*—Number: 60. Length: 8 mm.
- *Styles.*—Color: yellow-orange RHS 16B with some red RHS 182A. Length: 8 mm.
- *Stigmas.*—Color: yellow RHS 163C. Length: 2 mm.
- *Hips.*—None Observed.

PLANT CHARACTERISTICS

Plant form: Shrub.
Plant growth: Vigorous.
Age to maturity: Two years.
Mature plant: Height: 1 m 10 cm. Width: 1 m.
Rootstock: *Rosa* 'Dr. Huey' for U.S. and *Rosa dumetorum* cv. 'Laxa' for observed plants in the U.K.

Foliage:
- *Number.*—Leaflets on normal mid-stem leaves is: 7 (including terminal leaflet).
- *Size.*—Medium, about 13.5 cm long×9 cm wide.
- *Quantity.*—Normal. Number of leaves per flowering stem is: 10.
- *Color.*—New foliage: Upper side: bronze RHS 183B. Lower side: bronze RHS 183B. Old foliage: Upper side: green RHS 147A. Lower side: green RHS 147B.

Leaflets:
- *Size.*—About 7 cm long×4 cm wide.
- *Shape.*—Oval.
- *Base shape.*—Obtuse.
- *Apex shape.*—Acuminate.
- *Texture.*—Leathery.
- *Edge.*—Serrated.
- *Serrations.*—Double/Small.
- *Petiole.*—Color: yellow-green RHS 148C. Length: 2.5 cm. Width: 1.5 cm. Surface Texture: With prickles.
- *Petiole rachis.*—Color: yellow-green RHS 148C. Underside: with prickles.
- *Stipules.*—Length: 2 cm, serrated. Color: yellow-green RHS 148C.
- *Auricle.*—Shape: Pointed. Length: 4 mm. Width: 1 mm. Color: yellow-green RHS 148C.
- *Vein color.*—Green RHS 154D.
- *Venation pattern.*—Reticulate.

Wood:

*New wood.*—Color: bronze RHS 183B. Bark: Smooth.

*Old wood.*—Color: dark green RHS 144A. Bark: Smooth.

Branching habit:

*Number.*—8 per main stem.

*Lateral branch dimensions.*—Length: 40 cm. Diameter: 4 mm.

Stems:

*Mature stem.*—Length: 60 cm. Diameter: 6 mm.

*Internode distance.*—5 cm. The above measurements are all variable, depending on growing conditions in a season.

*Stem pubescence present.*—No.

Prickles:

*Quantity.*—On main canes from base: many. Number per stem length.—10 per 10 cm. On laterals from main canes: few. Number per stem length: 3 per 10 cm.

*Form.*—Deep concave.

*Length.*—5 mm.

*Color when young.*—Green-red RHS 182A.

*Color when mature.*—Green-red RHS 176A.

Small prickles:

*Quantity.*—Main stalk: None.

Disease resistance:

*Mildew.*—Resistant.

*Blackspot.*—Resistant.

*Rust.*—Resistant.

Pest resistance: Not tested.

Winter hardiness: Not tested.

Growing conditions: Normal.

What is claimed is:

1. A new and distinct variety of rose plant of the shrub class suitable for repeat flower production, substantially as herein shown and described.

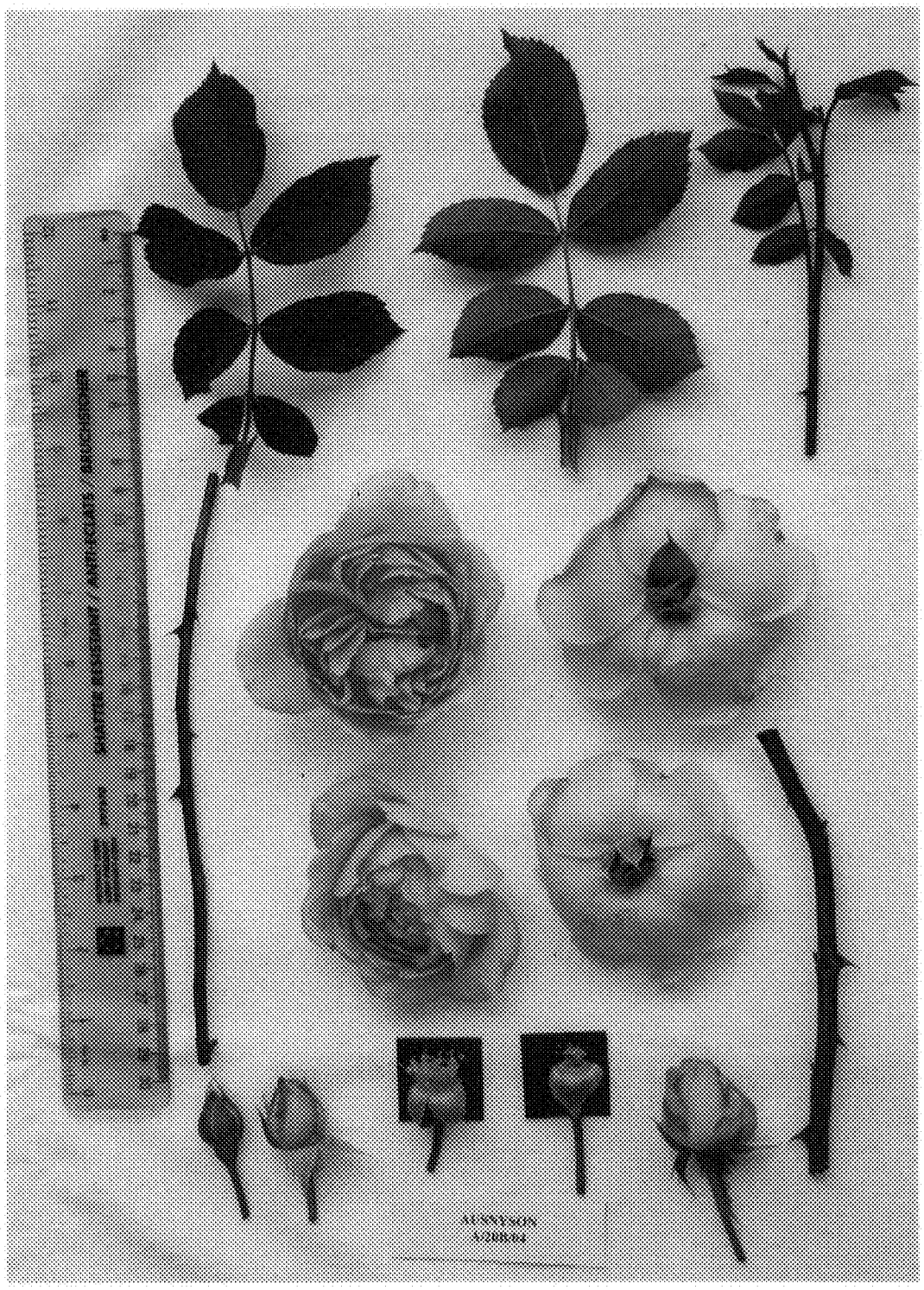

* * * * *